(12) United States Patent
Karrowni et al.

(10) Patent No.: US 12,369,935 B2
(45) Date of Patent: Jul. 29, 2025

(54) PERCUTANEOUS DEVICE FOR INTENTIONAL LACERATION OF ANTERIOR MITRAL VALVE LEAFLET

(71) Applicant: Kar Health, LLC, Iowa City, IA (US)

(72) Inventors: Wassef Karrowni, Cedar Rapids, IA (US); Mirna Karouni, Iowa City, IA (US)

(73) Assignee: Kar Health, LLC, Irvine, CA (US)

( * ) Notice: Subject to any disclaimer, the term of this patent is extended or adjusted under 35 U.S.C. 154(b) by 0 days.

(21) Appl. No.: 17/731,172

(22) Filed: Apr. 27, 2022

(65) Prior Publication Data
US 2022/0361908 A1    Nov. 17, 2022

Related U.S. Application Data

(60) Provisional application No. 63/180,298, filed on Apr. 27, 2021.

(51) Int. Cl.
A61B 17/32    (2006.01)
A61M 25/04   (2006.01)
A61B 17/00   (2006.01)

(52) U.S. Cl.
CPC ..... *A61B 17/320016* (2013.01); *A61M 25/04* (2013.01); *A61B 2017/00292* (2013.01); *A61B 2017/00783* (2013.01)

(58) Field of Classification Search
CPC .. A61B 17/320016; A61B 2017/00243; A61B 2017/00292; A61B 2017/00783; A61B 2017/00353; A61B 2017/00389; A61B 2017/320075; A61M 25/04; A61M 25/0026; A61M 25/0072; A61M 25/0155; A61M 25/06; A61M 25/09; A61M 25/10; A61M 2025/0079; A61M 2025/015; A61M 2025/09008
See application file for complete search history.

(56) References Cited

U.S. PATENT DOCUMENTS

| 5,397,333 | A | * | 3/1995 | Knoepfler | ...... | A61B 17/320016 |
|---|---|---|---|---|---|---|
| | | | | | | 606/167 |
| 2005/0192606 | A1 | * | 9/2005 | Paul, Jr. | ............. | A61B 17/3207 |
| | | | | | | 606/167 |
| 2008/0183080 | A1 | | 7/2008 | Abraham | | |
| 2010/0204662 | A1 | | 8/2010 | Orlov et al. | | |

(Continued)

FOREIGN PATENT DOCUMENTS

WO         9816161       4/1998
WO    WO-2020142758 A1 *  7/2020  .......... A61B 18/1445

OTHER PUBLICATIONS

Khan et al., "Transcatheter Electrosuergy: JACC State-of-the-Art Review", J Am Coll Cardiol., Mar. 31, 2020, pp. 1455-1470, vol. 75, No. 12.

*Primary Examiner* — Diane D Yabut
(74) *Attorney, Agent, or Firm* — Dentons Davis Brown; Kassandra Ricklefs (57) ABSTRACT

The disclosed apparatus, systems and methods relate to an anterior mitral valve leaflet laceration catheter. The catheter has a plurality of lumens so as to allow for the introduction of the device via a guide wire, the inflation of a balloon and the manipulation of an introducer having a curved distal end cutting portion that can be rotated into a charged position for the laceration of the anterior mitral valve leaflet.

7 Claims, 5 Drawing Sheets

(56) References Cited

U.S. PATENT DOCUMENTS

| | | |
|---|---|---|
| 2011/0060407 A1 | 3/2011 | Ketai et al. |
| 2014/0228871 A1* | 8/2014 | Cohen .............. A61B 17/32053 |
| | | 606/170 |
| 2016/0038722 A1* | 2/2016 | McLain ............ A61M 25/0194 |
| | | 606/159 |
| 2017/0027600 A1* | 2/2017 | McDonald ..... A61B 17/320783 |
| 2018/0206989 A1 | 7/2018 | O'Connell et al. |
| 2021/0085456 A1 | 3/2021 | Skarsgard |
| 2021/0346089 A1* | 11/2021 | Childs ............... A61M 25/0662 |

* cited by examiner

PERCUTANEOUS DEVICE FOR INTENTIONAL LACERATION OF ANTERIOR MITRAL VALVE LEAFLET

CROSS-REFERENCE TO RELATED APPLICATION(S)

This application claims priority to U.S. Provisional Application No. 63/180,298 filed Apr. 27, 2021 and entitled "Percutaneous Device for Intentional Laceration of Anterior Mitral Valve Leaflet," which is hereby incorporated by reference in its entirety under 35 U.S.C. § 119(e).

TECHNICAL FIELD

The disclosed technology relates generally to devices, systems and methods for the percutaneous laceration of the anterior mitral valve leaflet.

BACKGROUND

Figure 1A:
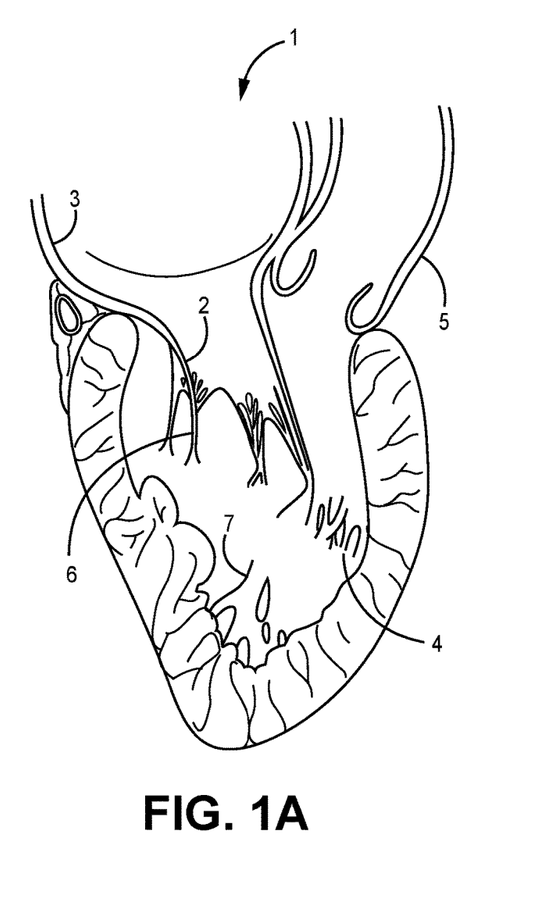
FIG. 1A is a cross-sectional view of a human heart, showing the mitral valve.
Figure 1B:
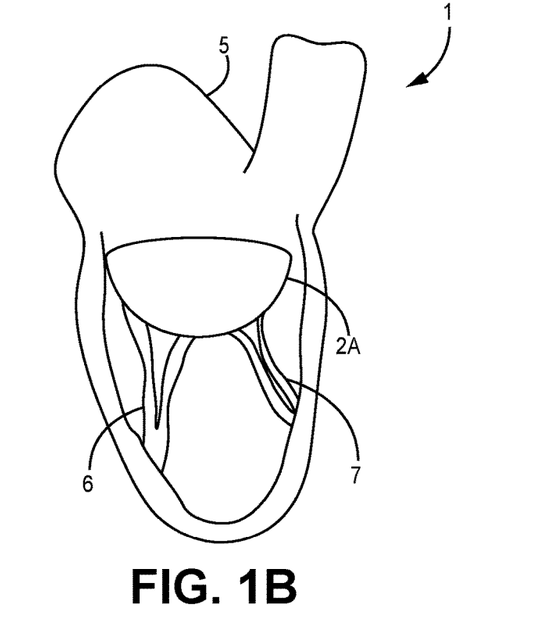
FIG. 1B is a schematic view of the human heart showing the anterior mitral valve leaflet.
Figure 1C:
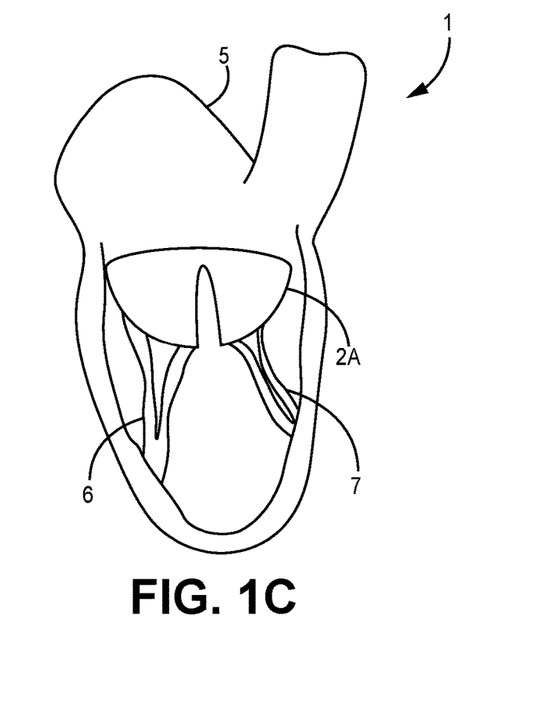
FIG. 1C is a schematic view of the human heart showing a split anterior mitral valve leaflet.

As shown in FIGS. 1A-1C, the heart's 1 mitral valve 2 is a very complex three-dimensional structure that separates the left atrium 3 from the left ventricle 4 and normally functions as a one-way valve. More specifically, the mitral valve 2 allows blood to flow from the left atrium 3 to the left ventricle 4 during the diastole part of the cardiac cycle and to prevent blood flow backward from the left ventricle 4 to the left atrium 3 during the systole part of the cardiac cycle. It is understood that the mitral valve 2 comprises several aspects, including the anterior mitral valve leaflet 2A. FIGS. 1A-1C further depict the aorta 5, chordae 6 and papillary muscles 7 for reference.

Transcatheter mitral valve replacement (TMVR) has emerged as an attractive less invasive approach to fix the diseased mitral valve 2 in patients who are unsuitable for surgical mitral valve repair or replacement due to a high risk of morbidity and mortality.

There are several dedicated devices for TMVR that are currently under development. Pending approval of those devices, transcatheter aortic valves which have proved safe and effective for treatment of aortic stenosis will be implanted in the mitral position. These would be in several clinical scenarios, including mitral bioprosthetic valve failures (valve-in-valve), failed prior mitral valve repairs with mitral annuloplasty ring in place (valve-in-ring), and in native mitral annular calcification, for example. However, even though these procedures are technically feasible, their success has been limited by the potential of left ventricular outflow tract (LVOT) obstruction. This is because there is a close relationship between the LVOT and the anterior leaflet 2A of the mitral valve 2, which can lead to LVOT obstruction in various pathologic scenarios or as complications in procedures. LVOT obstruction interferes with the ejection of blood from the left ventricle into the ascending aorta and subsequently body organs, leading to catastrophic consequences.

As such, the occurrence of LVOT obstruction as a complication of TMVR leads to poor outcomes and high in-hospital mortality. Its incidence varies from up to 10-40% of TMVR in mitral annular calcification, 5% of valve-in-ring, and 0.7-2% of valve-in-valve cases. Its mechanism is broadly divided into "fixed obstruction" or "dynamic obstruction". "Fixed obstruction" is caused by the anterior mitral leaflet of the native mitral valve being pushed towards the interventricular septum by the new transcatheter valve and thus causing narrowed and elongated LVOT. Pre-procedural CT scan screening could be used to try to predict the occurrence of what is known as fixed obstruction.

"Dynamic obstruction" is harder to predict, and its occurrence is related to systolic anterior motion of the anterior mitral leaflet towards the interventricular septum during systole, due to changes in flow characteristics and secondary Bernoulli forces generated by the change in the change in morphology of LVOT induced by TMVR. There is need to develop minimally invasive techniques to prevent LVOT obstruction or to treat it if it occurs as a complication of TMVR.

Recently a technique has been described for such use and is known LAMPOON (Laceration of the Anterior Mitral leaflet to Prevent Outflow ObtructioN). In this technique, and as shown in FIG. 1C, the anterior mitral valve leaflet 2A is intentionally split down the midline using focused radiofrequency energy directed by catheters and guidewires (as shown at 8 in FIG. 1C). For the purpose of preventing or relieving the LVOT obstruction, splitting 8 the anterior mitral valve leaflet 2A in the middle is desired compared to other locations since this maintains the integrity of the rest of the mitral valve apparatus (the papillary muscles 7 and the chordae 6) and might help in preserving the left ventricular function. The technique has been shown to be effective, however, it is technically very challenging and time consuming and relies on catheters and wires routinely used for other purposes and not dedicated for such a procedure. It also has its own risks since the laceration force is not very controlled and could lead to damage to nearby structures.

Thus, there is a need in the art for devices, systems and methods for performing splitting or laceration of the anterior mitral valve leaflet in a minimally invasive way and also in a fast, reproducible, and predictable fashion. This device should also be technically easy to use.

BRIEF SUMMARY

Discussed herein are various devices, systems and methods relating to a catheter or device for the splitting of the anterior mitral valve leaflet.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

In Example 1, an anterior mitral valve leaflet laceration catheter comprising: an elongate shaft comprising a plurality of lumens, and a positionable elongate introducer comprising a distal end cutting portion, wherein the elongate introducer is configured for the laceration of the anterior mitral valve leaflet via the distal end cutting portion.

In Example 2, the catheter of Example 1, wherein the plurality of lumens comprises a balloon lumen, a blade introducer lumen and a wire lumen.

In Example 3, the catheter of Example 1, wherein the distal end cutting portion is curved.

In Example 4, the catheter of Example 3, wherein the distal end of the cutting portion is curved and comprises a cutting surface.

In Example 5, the catheter of Example 1, wherein the cutting portion is configured to be selectively positionable in neutral and charged positions.

In Example 6, the catheter of Example 1, wherein the distal end cutting portion is configured to deliver controlled laceration force to target tissue.

In Example 7, the catheter of Example 1, wherein the cutting portion is configured to deliver controlled laceration force via mechanical force alone or in combination with transmittable energy.

In Example 8, a catheter for laceration of the anterior mitral leaflet, comprising: an elongate shaft defining a plurality of lumens, a wire, a balloon, and an introducer comprising a distal end cutting portion, wherein: the wire is configured for positioning of the catheter to a target location, the balloon is positioned on a side of the elongate shaft opposite the introducer, and the distal end cutting portion is curved.

In Example 9, the catheter of Example 8, wherein the distal end cutting portion comprises a cutting surface.

In Example 10, the catheter of Example 9, wherein the introducer is configured to be controlled by rotational movement of a knob disposed on a proximal end of the introducer.

In Example 11, the catheter of Example 10, wherein the distal end cutting portion is in rotational and translational communication with the knob.

In Example 12, the catheter of Example 11, wherein the distal end cutting portion is configured for selective positioning in neutral and charged positions.

In Example 13, a catheter for use in the laceration of the anterior mitral leaflet, comprising: an elongate shaft, a wire disposed through a wire lumen defined in the elongate shaft, a balloon disposed through a balloon lumen defined in the elongate shaft, and d an introducer comprising a knob and a distal end cutting portion, the introducer disposed through an introducer lumen defined in the elongate shaft, wherein the distal end cutting portion is in rotational and translational communication with the knob.

In Example 14, the catheter of Example 13, wherein the introducer lumen does not extend to the distal end of the elongate shaft.

In Example 15, the catheter of Example 14, wherein the distal end cutting portion is curved and configured to be rotated into a charged position via the knob.

In Example 16, the catheter of Example 15, wherein the distal end cutting portion comprises a cutting surface.

In Example 17, the catheter of Example 13, wherein the distal end cutting portion is configured to perform transcatheter electrosurgery.

In Example 18, the catheter of Example 13, wherein the balloon is in fluidic communication with one or more valves of a balloon device and is configured for inflation and deflation.

In Example 19, the catheter of Example 13, wherein the distal end cutting portion is configured to deliver controlled laceration force to target tissue.

In Example 20, the catheter of Example 13, wherein the elongate shaft is positionable via the guide wire.

Other embodiments of these Examples include corresponding computer systems, apparatus, and computer programs recorded on one or more computer storage devices, each configured to perform the actions of the methods. Implementations of the described techniques may include hardware, a method or process, or computer software on a computer-accessible medium.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

DETAILED DESCRIPTION

The various embodiments disclosed or contemplated herein relate to an anterior mitral valve leaflet (AMYL) laceration catheter or device 10 and associated systems and methods of use. Further, this and any of the other technologies described herein can be combined with any of the technologies taught or otherwise disclosed in Co-Pending U.S. application Ser. No. 16/047,626, filed Jul. 27, 2018, now U.S. Pat. No. 10,881,509, U.S. application Ser. No. 16/127,414 filed Sep. 11, 2018, now U.S. Pat. No. 10,737, 069, U.S. application Ser. No. 17/566,075 filed Dec. 30, 2021, and U.S. application Ser. No. 17/701,931 filed Mar. 23, 2022, each of which is hereby incorporated by reference in its entirety.

Figure 2A:
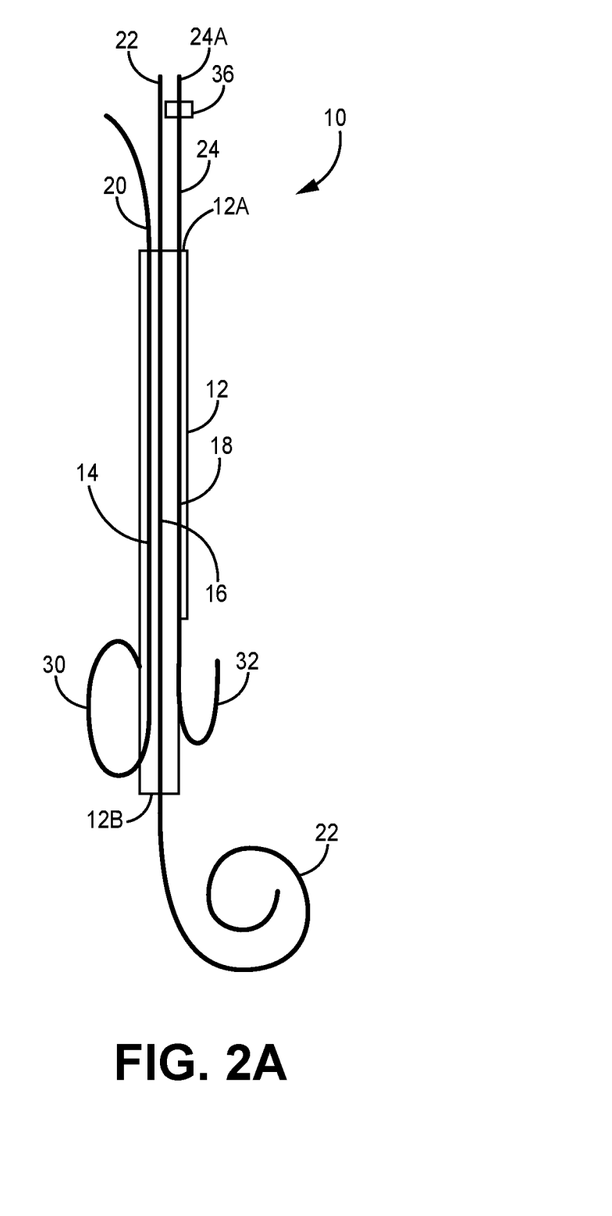
FIG. 2A is a side view of the device, according to one implementation.

As shown in FIG. 2A, the device 10 comprises an elongate shaft 12 comprising one or more lumens 14, 16, 18. in the implementation of FIG. 2A, a balloon lumen 14, guide wire lumen 16 and introducer lumen 18 are defined in the elongate shaft 12, as would be readily appreciated.

That is, in the implementation of FIG. 2A, the elongate shaft 12 defines a plurality of lumens 14, 16, 18 that extend from the proximal end 12A of the shaft to the distal end 12B, as would be readily appreciated. It is further contemplated and apparent from the implementation of FIG. 2A that certain of the lumens, here, the introducer lumen 18, do not extend to the same distal terminus 12B of the shaft 12. That is, one or more of the lumens 14, 16, 18 defined in the shaft 12 may end more proximally or distally relative to the others, so as to best accomplish the desired placement and operation of the device 10. As shown in the implementation of FIG. 2A, the introducer lumen 18 is not coterminal with the other lumens 14, 16, such that a distal end cutting portion 32 of the introducer 24 is disposed proximal to the distal ends of the other lumens 14, 16 (shown at 12B), as described further below.

Figure 2B:
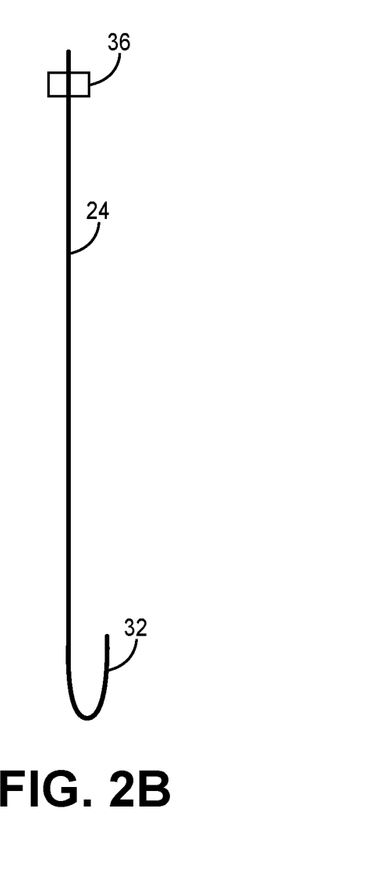
FIG. 2B is a side view of the blade introducer, according to one implementation.
Figure 2C:
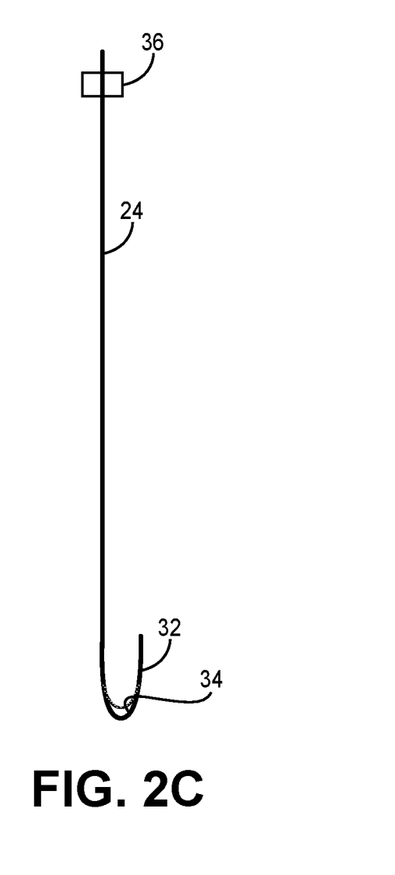
FIG. 2C is a side view of the blade introducer showing the blade cutting surface, according to one implementation.

Continuing with the implementation of FIG. 2A, the various lumens are sized to accommodate several devices for introduction into the surgical theater. That is, for example, a balloon device 20, guide wire 22 and introducer 24 can be used in conjunction with the various lumens 14, 16, 18 to accomplish the described procedures. It is appreciated that these components—balloon device 20, guide wire 22 and introducer 24—can be provided with the device 10 or introduced by the user, as would be understood. FIGS. 2B-2C depict further views of the introducer 24.

Figure 3A:
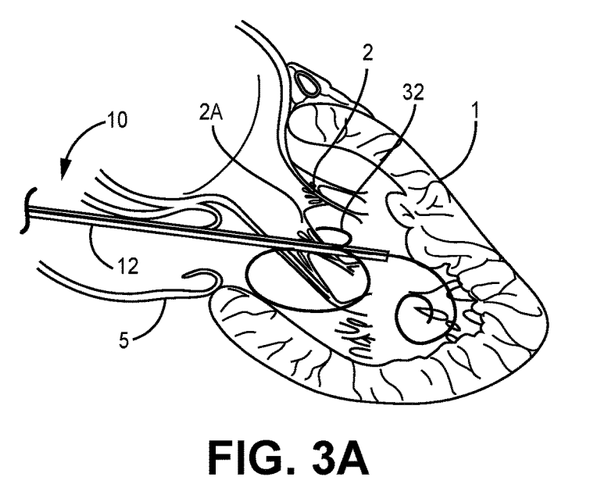
FIG. 3A is a side, cross-sectional view of the device introduced into the human heart, according to one implementation.
Figure 3B:
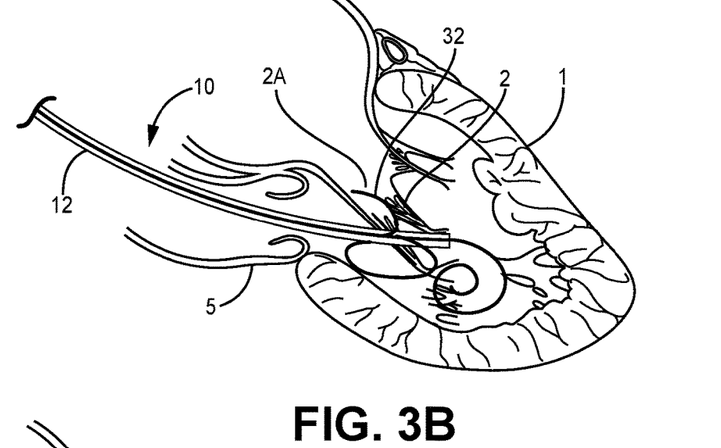
FIG. 3B is a side, cross-sectional view of the device of FIG. 3A introduced into the human heart and in the charged position and adjacent to the mitral valve leaflet, according to one implementation.
Figure 3C:
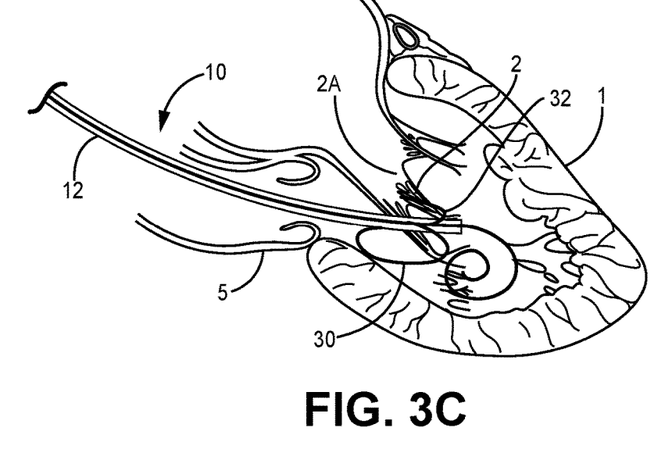
FIG. 3C is a side, cross-sectional view of the device of FIG. 3A introduced into the human heart and lacerating the mitral valve leaflet, according to one implementation.

The balloon device 20 comprises one or more valves 28 that are in fluidic communication with a distal balloon 30 that is in turn configured to be rapidly inflated or deflated by the valves 28 as would be readily understood, as is shown in the implementation of FIG. 2A. The balloon is sized in diameter and length depending on the anatomical characteristics of the left ventricle 4 and mitral valve 2 to be treated. The inflation of the balloon 30 can be used to help with orientation and approximation of the needle/blade to grab on the anterior mitral leaflet 2A, as shown in FIGS. 3A-3C. As is shown in FIG. 2A, in various implementations, the balloon lumen 14 is configured to open to the side of the shaft 12 for proper placement, as would be readily understood.

The balloon 30 can be made of nylon, silicone, polyurethane, or any other known material. Further, the size (diameter and length) of the balloon 30, can, according to certain embodiments, vary based on the physical dimensions of the individual patient. Alternatively, various versions of the device 10 can be provided with one or more balloons 30 of varying, predetermined sizes, as has been described in the incorporated references.

In various implementations, the balloon 30 is located at the distal end of the catheter 10, as described, and is inflated and deflated through the balloon lumen 14 inside the catheter that extends proximally outside of the body. The balloon 30 can be inflated using the standard procedures and using saline mixed with contrast or other suitable fluids understood by those of skill in the art.

In various implementations, the balloon 30 can have various shapes or forms. For example, in one implementation it is circular, or wheel-shaped, optionally with a space defined within, so as to allow continued uninterrupted blood flow during balloon 30 inflation in the left ventricle 4. It is appreciated that the balloon 30 in the various implementations discussed herein is in fluidic communication with an external operations unit configured to apply or reduce fluidic pressure, such as compressed air or via the introduction of a fluid as is well understood and appreciated in the art.

In use, the balloon 30 is configured to be positioned in the left ventricle 4 against the interventricular septum, such that when inflated to the desired volume, the balloon 30 helps orient the distal end cutting portion 32 to the correct orientation facing the anterior mitral leaflet 2A and also approximated the needle/blade tip to facilitate grabbing the leaflet, as is shown in FIGS. 3A-3C.

Continuing with the implementations of FIG. 2A-C, the wire 22 further extends through the length of the shaft 12 and beyond the distal shaft end 12B so as to be usable in the theater as well, as described below such as in reference to FIGS. 3A-3C.

Further, in the implementation of FIGS. 2A-2C, the introducer 24 further comprises a distal cutting portion 32 such as a needle or blade portion 32 configured to lacerate the mitral valve (shown in FIG. 2A-C at 8). In various implementations, and as shown in FIGS. 2B-2C, the introducer 24 comprises a cutting edge portion 32 that is positionable. The cutting edge portion 32 can, in various implementations, comprise a sharpened or honed cutting surface 34 inside its inner curvature, as is shown and would be readily understood. In various implementations, the introducer 24 is made of stainless steel, cobalt-chrome alloy, titanium, or nickel-titanium alloy (nitinol), though other materials are of course possible.

The introducer 24 is configured to traverse the introducer lumen 18 of the catheter 10 with the proximal end remaining outside the body and having an optional control 36 used to control the distal end cutting portion 32, which is optionally curved such that the cutting surface 34 is enclosed by the curved J- or U-shaped distal end cutting portion 32 (shown, for example, in FIGS. 2B-2C), which aids in the capture of the anterior mitral leaflet 2A. It is understood that in various implementations the control is achieved using a knob by either push/pull orientation or rotational movement. In various implementations of the device 10, the cutting portion 32 is disposed opposite the balloon, that is, on the "front" side of the catheter 10 opposite to the orientation of the balloon 30 on the "back" side.

It is understood that the cutting portion 32 is positionable during use, such that it can be in several positions, such as a charged position (FIG. 3A-3B and FIG. 4F-4G) with the distal end cutting portion 32 protruding out or perpendicular to the catheter surface for use in grabbing on the leaflet and transmitting mechanical and/or electrosurgical cutting force or a neutral position (FIG. 4D-4E) where the cutting surface 34 is concealed to avoid unintentional damage of tissue during the introduction of removal of the catheter, or during the orientation of the catheter to the correct position inside the left ventricle 4.

As shown in FIGS. 3A-3C, in various implementations, the device 10 can be delivered through an artery through a sheath using standard techniques, certain non-limiting examples being the femoral, radial, brachial, axillary or carotid arteries. Others would be appreciated by those of skill in the art. In various implementations, the introduction is performed under guidance using X-ray (fluoroscopy) and/or ultrasound (echocardiography 2D and/or 3D), as would also be appreciated from the present disclosure. It is understood that during use, the switch of the position of the cutting portion 32 between neutral and charged can be accomplished by rotational force/by the control knob 36 on the proximal end 24A of the introducer 24 or by push/pull force.

In use according to various implementations, the device 10 is therefore introduced over the wire 22 threaded through the wire lumen 16 of the catheter 10 and guided over the wire 22 into the left ventricle 4 through the aortic valve 5 or through other standard approaches (apex of the left ventricle or transeptal).

In use according to certain implementations and as shown in FIGS. 3A-3C, lacerating or cutting of the anterior mitral leaflet 2A can be induced or facilitated by mechanical operations, such as pulling on the cutting portion 32 of the device 10 or by connecting the proximal end 24A of the introducer 24 to energy source (not shown) in order to perform transcatheter electrosurgery using the standard technique, where radiofrequency energy is used to vaporize and lacerate tissue, such as the leaflet 2A. It is appreciated that in certain situations, this vaporization and/or laceration can be achieved despite flowing blood. As such, in various implementations, the cutting portion 32 is in electronic communication with an electrical system having an energy source (not shown) configured to provide electricity to the cutting portion, as would be understood.

In various implementations, and as shown in FIGS. 4B-4G, the distal end 12B of the catheter 10 is semicircular, with the flat end having two optional indentations or depressions 18A, 18B being used as a surface to lay the cutting portion 32 when in its neutral position, as would be understood. Further, the distal end 12B of the catheter 10 in various implementations can be manipulated to change its angle which would help in the approximation of the cutting portion 32 to the anterior mitral leaflet.

Figure 4A:
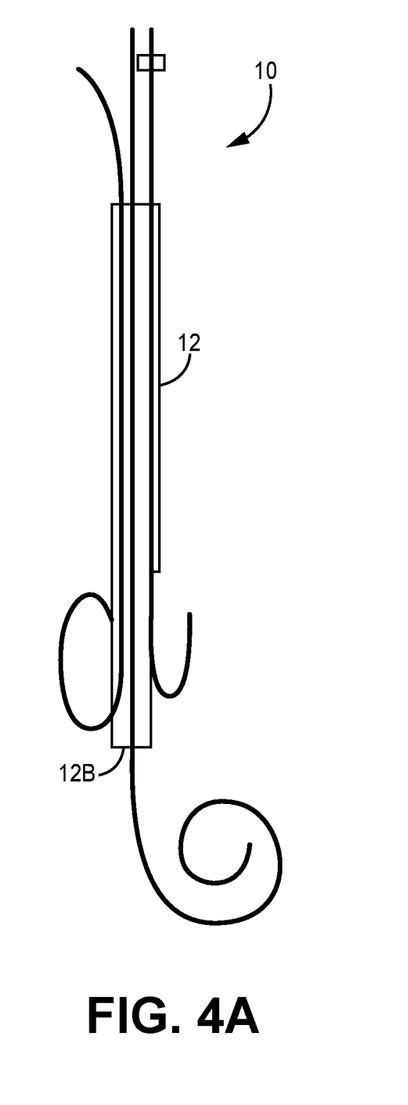
FIG. 4A is a side view of the device, according to a further implementation.
Figure 4B:
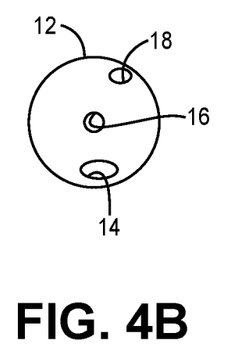
FIG. 4B is a cross-sectional view of the shaft of the device, according to one implementation.
Figure 4C:
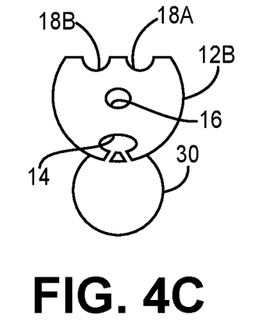
FIG. 4C is a cross-sectional view of the distal end of the shaft of the device, showing the balloon, according to the implementation of FIG. 4B.
Figure 4D:
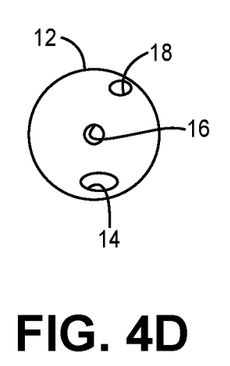
FIG. 4D is a cross-sectional view of the shaft of the device, according to one implementation.
Figure 4E:
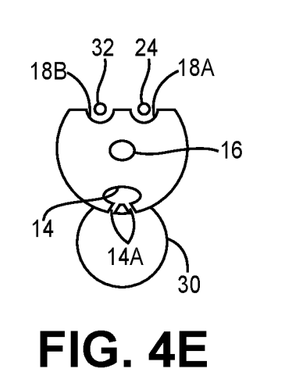
FIG. 4E is a cross-sectional view of the distal end of the shaft of the device, showing the balloon, according to the implementation of FIG. 4D.
Figure 4F:
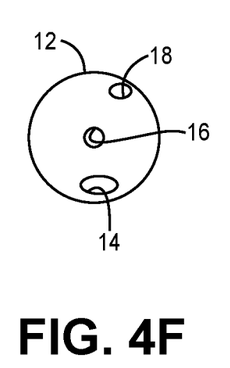
FIG. 4F is a cross-sectional view of the shaft of the device, according to one implementation.
Figure 4G:
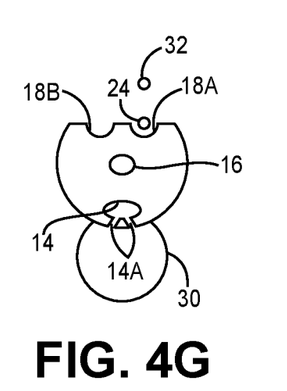
FIG. 4G is a cross-sectional view of the distal end of the shaft of the device, showing the balloon, according to the implementation of FIG. 4F.

In use, during advancement of the catheter 10 through a vessel to the target position, the cutting portion 32 would be in the neutral position inside the depressions 18A, 18B on the semicircular surface of the distal end 12B, as shown in FIG. 4C. Thus, the cutting portion 32 would be advanced to target position without unintentional damage or injury to the vessel or the surrounding structures.

Once the catheter is at the target position, the cutting portion 32 can be oriented to be charged or perpendicular to the semicircular distal end 12B and thus protruding out in order to grasp the tissue to lacerate, or the anterior mitral leaflet in this case, and subsequently deliver the energy to lacerate the tissue. After completion of the intentional laceration, the cutting portion 32 can be rotated back to the neutral position and thus the catheter 10 could be safely removed outside the body without inflicting any unintentional damage to tissue during this process.

Continuing with the implementations of FIG. 4B-4G, in various implementations, the balloon lumen 14 can have one or more openings 14A configured to allow for the rapid inflation/deflation of the balloon 30, as would be understood.

Further, the inflation of the balloon 30 followed by grabbing and splitting the anterior mitral leaflet could be facilitated by rapid pacing of the heart, or inducing a pause for few seconds using standard techniques.

Although the disclosure has been described with reference to preferred embodiments, persons skilled in the art will recognize that changes may be made in form and detail without departing from the spirit and scope of the disclosed apparatus, systems and methods.

What is claimed is:

1. A catheter for use in the laceration of the anterior mitral leaflet, comprising:
   a. an elongate shaft comprising at least one depression on a distal end;
   b. a wire disposed through a wire lumen defined in the elongate shaft;
   c. a balloon disposed through a balloon lumen defined in the elongate shaft on a first side of the elongate shaft; and
   d. an introducer comprising a knob and a distal end cutting portion, the introducer disposed through an introducer lumen defined in the elongate shaft on a second side of the elongate shaft,
   wherein the distal end cutting portion is curved and comprises a cutting surface on an inner portion of the curvature, wherein the distal end cutting portion is in rotational and translational communication with the knob and wherein the distal end cutting portion is configured to be positioned within the at least one depression.

2. The catheter of claim 1, wherein the introducer lumen does not extend to the distal end of the elongate shaft.

3. The catheter of claim 2, wherein the distal end cutting portion is configured to be rotated into a charged position via the knob.

4. The catheter of claim 1, wherein the distal end cutting portion is configured to perform transcatheter electrosurgery.

5. The catheter of claim 1, wherein the balloon is in fluidic communication with one or more valves of a balloon device and is configured for inflation and deflation.

6. The catheter of claim 1, wherein the distal end cutting portion is configured to deliver controlled laceration force to target tissue.

7. The catheter of claim 1, wherein the elongate shaft is positionable via the guide wire.

* * * * *